US00PP14197P39

(12) United States Plant Patent
Anderson et al.

(10) Patent No.: US PP14,197 P3
(45) **Date of Patent: *Oct. 7, 2003**

(54) CHRYSANTHEMUM PLANT NAMED MN 92-333-2

(50) Latin Name: *Chrysanthemum hybrid*
Varietal Denomination: MN92-333-2

(75) Inventors: Neil Owen Anderson, St. Paul, MN (US); Peter David Ascher, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/503,271

(22) Filed: Feb. 14, 2000

(65) Prior Publication Data

US 2003/0126661 P1 Jul. 3, 2003

(51) Int. Cl.[7] ..... A01H 5/00
(52) U.S. Cl. ..... Plt./298
(58) Field of Search ..... Plt./298

(56) References Cited

U.S. PATENT DOCUMENTS

| | | | |
|---|---|---|---|
| PP7,513 | P | 4/1991 | VandenBerg |
| PP7,754 | P | 12/1991 | VandenBerg |
| PP8,759 | P | 5/1994 | VandenBerg |
| PP9,445 | P | 1/1996 | VandenBerg |
| PP10,848 | P | 4/1999 | VandenBerg |
| PP10,909 | P | 5/1999 | Wain |
| PP10,943 | P | 6/1999 | Fuess |
| PP11,009 | P | 7/1999 | Davino, Jr. |
| PP11,032 | P | 8/1999 | Glicenstein |

OTHER PUBLICATIONS

Peter Ascher, et al., Maxi–Mums A Horticultural Breakthrough!, Minnesota Report 242–1997 University of Minnesota, Distribution Center Publication MR–67280B Minnesota Agricultural Experiment Station University of Minnesota (1997).
R.B. Clark, History of Culture of Hardy Chrysanthemums, National Chrysanthemum Society 18(3):144, 1962.
W.W. Garner, et al., Flowering and Fruiting of Plants as Controlled By The Length Of Day, 1920, p. 377–400, Yearbook of the Department of Agriculture, 1920, USA.
Peter Ascher, et al., Breeding and New Cultivars, Academic Perspective, Tips on Growing and Marketing Garden Mums, Ohio Florist's Association 1996.
Bradford Bearce, et al., Chrysanthemums A Manual of the Culture, Diseases, Insects and Ecocomics of Chrysanthemums, Jun. 1964, pp. 6–19, Prepared for The New York State Extension Service Chrysanthemum School with the Cooperation of the New York State Flower Growers Association, Inc.
Neil O. Anderson, et al., Rapid Generation Cycling of Chrysanthemum Using Laboratory Seed Development and Embryo Rescue Techniques, Journal of the American Society of Horticultural Science, Mar. 1990, pp. 329–336, vol. 115(2), Alexandria, Virginia 22314.
Leon Glicenstein, Breeding and New Cultivars, Commercial Perspective, Tips on Growing and Marketing Garden Mums, Ohio Florist's Association 1996.
M.A. Nazeer, et al., Cytyogenetical Evolution of Garden Chrysanthemum, Current Science, Jun. 20, 1982, Vo. 51, No. 12.
Edward Higgins, Containers and Marketing, Tips on Growing and Marketing Garden Mums, Ohio Florist's Association 1996.
Naomasa Shimotomai, Bastardierungsversuche bei Chrysanthemum I., Journal of Science of the Hiroshima University, Series, B, Div. 2, vol. 1, Art. 3, 1931.
Naomasa Shimotomai, Bastardierungsversuche bei Chrysanthemum II. Eentstehung eines fruchtbaren Bastardes (haploid $4n^2$) aus der Kreuzung von *Ch. marginatum* (hapl. 5n) mit *Ch. morifolium* (hapl. 3n), Journal of Science of the Hiroshima University, Series B, Div. 2, vol. 1, Art. 8, 1932.
Ernest L. Scott, The Breeder's Handbook, 1957, pp. 1–76Handbook No. 4, National Chrysanthemum Society, Inc., U.S.A.
John Woolman, Chrysanthemums For Garden And Exhibition, 1953, pp. 1–103, W.H. & H. Collingridge Ltd., Tavistock Street, London WC2 and Transatlantic Arts Incorporated, Forest Hills, New York.
H.G. Witham Fogg, Chrysanthemum Growing, 1962, pp. 1–171, John Gifford Limited, London, W.C.2.
National Agricultural Statistics Service, USDA Additional Floriculture Information, pp. 1–64, National Agricultural Statistics Service, Floriculture Crops, 1998 Summary, Jun. 1999.
Handbook on Chrysanthemum Classification, A publication of the Classification Committee National Chrysanthemum Society, Inc. U.S.A., 1996 Edition.
C. Ackerson, Chapter 12 Development of the Chrysanthemum in China, pp. 146–155, National Chrysanthemum Society Bulletin 1967.
C. Ackerson, Chapter 11 Original Species of the Chrysanthemum, pp. 105–107, National Chrysanthemum Society Bulletin 1967.
G.J. Dowrick, The Chromosomers of Chrysanthemum, I: The Species, pp. 365–375, 1952.

*Primary Examiner*—Bruce R. Campell
*Assistant Examiner*—Annette H. Para
(74) *Attorney, Agent, or Firm*—Wood, Phillips, Katz, Clark & Mortimer

(57) ABSTRACT

A new and distinct Chrysanthemum plant named MN92-333-2 is provided.

4 Drawing Sheets

BACKGROUND OF THE INVENTION

The present invention comprises a new and distinctive chrysanthemum plant, hereinafter referred to by the cultivar name MN92-333-2. This new cultivar was the result of a cross in 1989 between *Chrysanthemum weyrichii* and *Chrysanthemum morifolium.* More specifically, the breeding program which resulted in the production of the new cultivar was carried out at St. Paul, Minn. The female or seed parent of 92-333-2 was a *Chrysanthemum weyrichii,* commercially available from White Flower Farms, Conn. having the following characteristics: (a) the plant habit is prostrate and the plant spreads via rhizomes to form a large mat after the first year; (b) the plant dimensions are that the plant has a diameter of about 1.5' and is about 5–6" tall; (c) the plant is hardy in zones 4–9 (Southeast)/Zone 10 (west); (d) the flower of the plant is a single daisy, having light lavender-colored ray florets and central disc florets with yellow pollen; (e) the plant has leaves that are dark green in color, with a very shiny leaf surface (glossy), and glabrous leaf margins that are deeply incised; and (d) the plant tends to rosette, needs cold treatment to flower consistently, flowering can be sporadic with gaps in the plant architecture and the plant is an obligate short-day plant. The male or pollen parent of 92-333-2 was a *Chrysanthemum morifolium* which is commercially available from Yoder Brothers, Inc., Barberton, Ohio having the following characteristics: (a) the plant habit is cushion; (b) the plant dimensions are that the plant is similar to other cushion types commercially available from Yoder Brothers, Inc., such as, but not limited to the variety, 'Raquel'; (d) the plant is hardy in zones 6–9 (Southeast)/Zone 10 (west); (d) the flower is a single or duplex daisy, possibly orange or bronze ray florets, central disc florets with yellow pollen; (e) the plant has leaves that are similar to other Yoder Brothers, Inc. cushion series chrysanthemums; and (d) the plant is a facultative short-day plant. The resulting seed, identified as 90-287-16 was collected. In 1991, a plant of 90-287-16 was crossed as the male parent with plants identified as 90-147-10, a University of Minnesota inbred parental selection, as the female parent and the resulting seeds, identified as cross number 92-333 were collected. In 1992, plants of 92-333 were germinated and flowering progeny evaluated. 92-333-2 was the second plant from the cross and was selected during the fall of 1992. The parentage of the new cultivar can be summarized as follows:

*Chrysanthemum weyrichii*×*Chrysanthemum morifolium*

Asexual reproduction of the new cultivar by terminal or stem cuttings taken 1993 through 1999 at St. Paul, Minn., U.S.A. has demonstrated that the characteristics of the new cultivar as herein described are firmly fixed and are retained through successive generations of such asexual propagation.

SUMMARY OF INVENTION

It was found that the cultivar of the present invention:

(a) exhibits extreme hybrid vigor, (b) develops, in its second and subsequent years after planting, when grown in the fall under natural day-length and without the application of growth regulators, into a flowering herbaceous shrub having a plant height of from about 3.0 to about 3.75 feet and a spread from about 3.7 to about 6.0 feet, (c) exhibits, in its second and subsequent years after planting and during the fall season (August-October), a massive floral display, (d) displays flowers which are slightly toned with grey, giving the flower petals a slightly altered coloration, (e) exhibits superior winter hardiness, including frost tolerance, (f) exhibits self-pinching, and (g) exhibits a less facultative, short-day response.

The 92-333-2 cultivar has not been observed under all possible environmental conditions to date. Accordingly, it is possible that the phenotype may vary somewhat with variations in the environment, such as temperature, light intensity, and day length.

When the new cultivar of the present invention is compared to 'Empire Salsa' (U.S. Plant Pat. No. 9,578, it is found to exhibit a more spreading and prolific habit accompanied with a massive floral display in its second and subsequent years after planting. Reference is made to Table 1 below which compares certain characteristics of 92-333-2 to 'Empire Salsa'.

TABLE 1

| CHARACTERISTIC | 92-333-2 | 'Empire Salsa' |
|---|---|---|
| Capitulum form and type | Duplex/triplex daisy | Flat daisy |
| Plant Height | About 1.8 to 2.0 feet (first year) About 3.0 to 3.75 feet (Second year) | 9 to 11 inches |
| Branching Pattern | Spreading and very prolific | Spreading |
| Flowering Response | 6 weeks | 7 weeks |
| Flower diameter | 60 to 9 cm | 6 to 6.4 cm |
| Ray florets, color, mature | Red | Red-purple |

BRIEF DESCRIPTION OF THE PHOTOGRAPHS

The accompanying photographs show as nearly true as it is reasonably possible to make the same in color illustrations of this type, typical flower and foliage characteristics of the new cultivar. The plants were grown in a greenhouse at St. Paul, Minn., USA.

FIG. 1 shows an adaxial and abaxial views of the leaf shape of chrysanthemum variety 92-333-2.

FIG. 3 is a color photograph of chrysanthemum variety 92-333-2 after one year of growth.

FIG. 4 is a color photograph of chrysanthemum variety 92-333-2 after two years of growth.

DETAILED BOTANICAL DESCRIPTION

Figure 2:
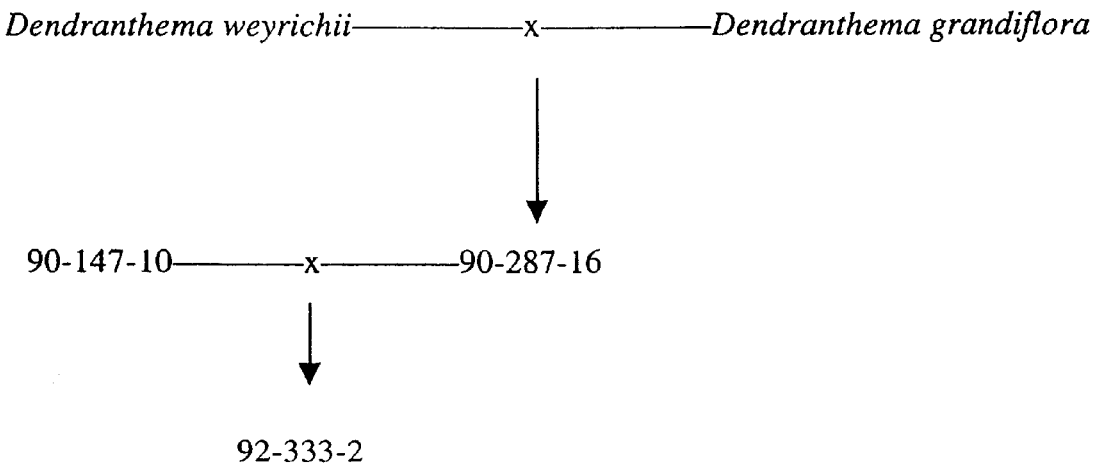
FIG. 2 shows the breeding history of chrysanthemum variety 92-333-2.

The chart used in the identification of colors described herein is The R.H.S. Colour Chart of The Royal Horticultural Society, London, England. The color values were determined on Jan. 13, 2003 in St. Paul, Minn. The readings were taken between 11:00 and 1:00 p.m. under approximately 2500 footcandles of light. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type.*—Herbaceous stem cutting.

*Time to rooting.*—About 1 week.

*Rooting habit.*—Vigorous.

Botanical classification: Chrysanthemun hybrid cv. 'MN92-333-2'.

Commercial classification: Chrysanthemum hybrid.

Plant description:

*Appearance, shape.*—Mounded, spherical.

*Appearance, growth habit.*—Mound.

*Appearance, growth rate/vigor.*—Vigorous.

*Plant height.*—About 1.8 to about 2.0 feet (first year) about 3.0 to about 3.75 feet (second year).

*Lateral branch length.*—0.5 to 3 feet.

*Quantity of lateral branches after removal of apical meristem.*—One per node.
*Stem color.*—RHS Green Group 138B.

Foliage description:
*Number of leaves per plant.*—Greater than about 3,000.
*Number of leaves per lateral branch.*—3 to 25.
*Leaf arrangement.*—Alternate.
*Leaf size, fully expanded, length.*—5 cm.
*Leaf size, fully expanded, width.*—4 cm.
*Leaf apex.*—Acute.
*Leaf base.*—Truncate to auriculate.
*Leaf margin.*—Incised.
*Leaf textures.*—Glaucous/hirsute.
*Petiole length.*—3 to 5 cm.
*Color, young foliage adaxial surface.*—RHS Green Group 138A.
*Color, young foliage abaxial surface.*—RHS Green Group 138C.
*Color, fully expanded foliage adaxial surface.*—RHS Green Group 135B.
*Color, fully expanded foliage abaxial surface.*—RHS Green Group 141B.
*Color, venation adaxial surface.*—RHS Green Group 138B.
*Color, venation abaxial surface.*—RHS Green Group 138C.
*Color, petiole.*—RHS Green Group 138C.

Phyllary description:
*Appearance.*—The involucral bracts (phyllaries) are crenulate.
*Color.*—RHS Green Group 138C.
*Texture.*—Glabrous.
*Size.*—Approximately 0.2–0.4 cm in length.

Inflorescence description:
*Appearance.*—Head (composite); duplex/triplex daisy.
*Flowering response.*—6 weeks (SD).
*Quantity of inflorescences.*—About 5,000 (second year).
*Inflorescence size, diameters.*—6 to 9 cm.
*Inflorescence size, depth (height).*—2 to 3 cm.
*Inflorescence size, diameter of disc.*—1.2 to 3 cm.
*Opening inflorescences, bud shape.*—Upright, tubular.
*Opening inflorescences, bud size, length.*—1.75 to 2 cm.
*Opening inflorescences, bud size, width.*—1.25 to 1.8 cm.
*Opening inflorescences, bud color.*—RHS Red Purple Group 60D.
*Ray florets, shape.*—Daisy.
*Ray florets, size, length.*—2.1 to 3 cm.
*Ray florets, size, width.*—0.75 to 0.9 cm.
*Ray florets, apex.*—Obtuse.
*Ray florets, base.*—Cuneate.
*Ray florets, margins.*—Entire.
*Ray florets, texture.*—Glabrous.
*Ray florets, aspect.*—Horizontal to slightly pendant.
*Number of ray florets per inflorescence.*—About 68 to about 72.
*Ray florets, color, when opening, adaxial surface.*—RHS Red Purple Group 60.
*Ray florets, color, when opening, abaxial surfaces.*—RHS Red Purple Group 74.
*Ray florets, color, mature, adaxial surfaces.*—RHS Red Group 53C.
*Ray florets, color, mature, abaxial surface.*—RHS Purple Group 78D.
*Ray florets, color, fading to.*—RHS Red Group 40D.
*Disc florets, shape.*—Tubular, rounded at tip.
*Disc florets, size, length.*—0.4 cm (unopened) 0.4 cm (opened).
*Disc florets, size, width.*—0.1 cm (unopened) 0.2 cm (opened).
*Number of disc florets per inflorescence.*—About 120.
*Disc florets, color, immature.*—RHS Yellow Orange Group 16A.
*Disc florets, color, mature.*—RHS Yellow Orange Group 15B.
*Peduncle, aspect, strength.*—Stiff.
*Peduncle, aspect, angle to stem.*—45.
*Peduncle, length, first peduncle.*—3.2 cm.
*Peduncle, length, fourth peduncle.*—8.4 cm.
*Peduncle, texture.*—Ribbed, mildly hirsute.
*Peduncle, color.*—RHS Green Group 138A.
*Reproductive organs, androecium, floret location.*—Disc florets.
*Anther colors.*—RHS Yellow Orange Group 21B.
*Pollen, abundance.*—Abundant.
*Pollen, color.*—RHS Yellow Orange Group 21A.
*Reproductive organs, gynoecium, floret location.*—Disc/ray florets.
*Style color.*—RHS Yellow Orange Group 7A.

Disease resistance: MN-92-333-2 has not been tested for any disease suspectibility, tolerance or resistance.

Seed production and fruit: About 192 ovules/flower. The fruit is an achene, a dry, indehiscent fruit with a single locule and a single seed, and with the seed attached to the ovary wall at a single point. The achene does not have any pappus of awns for bristles; its general shape is a half-inflated football oval with pointed ends. Seed size is about 0.2–0.5 cm in length and about 0.1–0.2 cm in width. The surface texture is ridged. The color designation for the seed is RHS Brown Group 200D.

Winter hardiness: Hardy in zones 3–10 in uncovered field conditions without the need for added protection such as snow fences, mulch, etc.

Frost tolerance: Yes, extends blooming season to the first freeze in the north (In zones 3–4 the first frost usually takes place between September 1–15. In zones 3–4, the first freeze usually takes place between October 1–20).

Fragrance: Fragrance is noticeable when handling or bruising the foliage.

Longevity of the bloom: Flower longevity is temperature dependent. Under normal conditions in the field, during the fall season, flowers will typically last about 2–4 plus weeks.

What is claimed is:

1. A new and distinct plant as herein described and illustrated.

* * * * *